United States Patent [19]

Edgar et al.

[11] Patent Number: 4,677,975
[45] Date of Patent: Jul. 7, 1987

[54] METHOD OF DISPENSING AND/OR A DISPENSER

[75] Inventors: Brian W. Edgar; Robert B. Elliott, both of Auckland, New Zealand, 4

[73] Assignee: The University of Auckland, Auckland, New Zealand

[21] Appl. No.: 788,030

[22] Filed: Oct. 16, 1985

[30] Foreign Application Priority Data

Oct. 16, 1984 [NZ] New Zealand .................. 209900

[51] Int. Cl.$^4$ .................................... A61M 16/00
[52] U.S. Cl. ........................... 128/200.14; 128/204.23
[58] Field of Search ................ 128/200.14, 200.15, 128/200.16, 200.17, 200.18, 200.21, 200.23, 203.15, 203.12, 203.13, 203.14, 204.21, 204.23, 205.23, 716, 719, 724, 725; 272/99 R

[56] References Cited

U.S. PATENT DOCUMENTS

| | | | |
|---|---|---|---|
| 3,726,270 | 4/1973 | Griffis et al. .................. | 128/719 |
| 4,106,503 | 8/1978 | Rosenthal et al. ............. | 128/200.18 |
| 4,109,656 | 8/1978 | Goethel et al. ................ | 128/203.15 |
| 4,174,712 | 11/1979 | Moren et al. .................. | 128/200.14 |
| 4,206,644 | 6/1980 | Platt ............................... | 128/204.23 |
| 4,253,468 | 3/1981 | Lehmbeck ..................... | 128/200.18 |
| 4,357,936 | 11/1982 | Ellestad et al. ................ | 128/204.23 |
| 4,462,398 | 7/1984 | Durkan et al. ................. | 128/204.23 |

Primary Examiner—Henry J. Recla
Attorney, Agent, or Firm—Holman & Stern

[57] ABSTRACT

A method and apparatus for dispensing inhalable material includes the steps of indicating to a patient that a breath should be taken, detecting the start of inhalation, causing inhalable material to be supplied to the air passages of the patient during a preselected part of the period of inhalation, then after a predetermined inhalation period substantially preventing further inhalation, indicating to the patient that exhalation should begin, detecting the start of exhalation, and after a predetermined exhalation period again indicating that a breath should be taken. The dispenser includes a supply of inhalable material, a mouthpiece, and a control device for selectively controlling the flow between the supply and the mouthpiece, as well as between the supply and the atmosphere. The device also includes a signalling means for indicating to the user when to inhale and subsequently when to exhale. Also included is a detection device to detect commencement of inhalation and to start a timer, as well as a second detection device to detect commencement of exhalation and to cause a second timer to start, to time a predetermined exhalation period.

16 Claims, 4 Drawing Figures

METHOD OF DISPENSING AND/OR A DISPENSER

BACKGROUND OF THE INVENTION

This invention relates to a method of dispensing and/or a dispenser.

Current dispensers of in particular inhalable material in aerosol form require the aerosol generating mechanism (such as a nebulizer) to operate in an inefficient mode and this results in different sized doses as the size of the dose depends upon how the generating mechanism is used. This is wasteful of the drug and the variablility in dose size can result in under or over dosing.

SUMMARY OF THE INVENTION

It is therefore an object of the present invention to provide a method of dispensing and/or a dispenser which will obviate or minimise the foregoing disadvantages in a simple yet effective manner or which will at least provide the public with a useful choice.

Accordingly in one aspect the invention consists in a method of dispensing inhalable material comprising the steps of indicating to a patient that a breath should be taken, detecting the state of breathing, and causing or allowing said inhalable material to be supplied to the mouth or nose of the patient during a selected part of the period of inspiration.

In a further aspect the invention consists in a dispenser comprising a supply means to supply inhalable material in inhalable form, said supply means being in connection with atmosphere and a mouth or nose piece, flow control means to allow or substantially prevent flow between said supply means and said mouth or nose piece and said supply means and said atmosphere, signalling means to indicate to the user when to inhale, detection means to detect the commencement of inspiration and/or expiration and to cause said flow control means to cause or allow said inhalable material to move from said supply means to said mouth or nose piece during a selected part of the period of inspiration.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the invention will now be described with reference to the accompanying drawings in which.

FIG. 5 shows a sensor arrangement for detecting a position of an element;

FIG. 6 shows schematically an alternative embodiment of a sensing device.

DETAILED DESCRIPTION OF THE INVENTION

Figure 1:
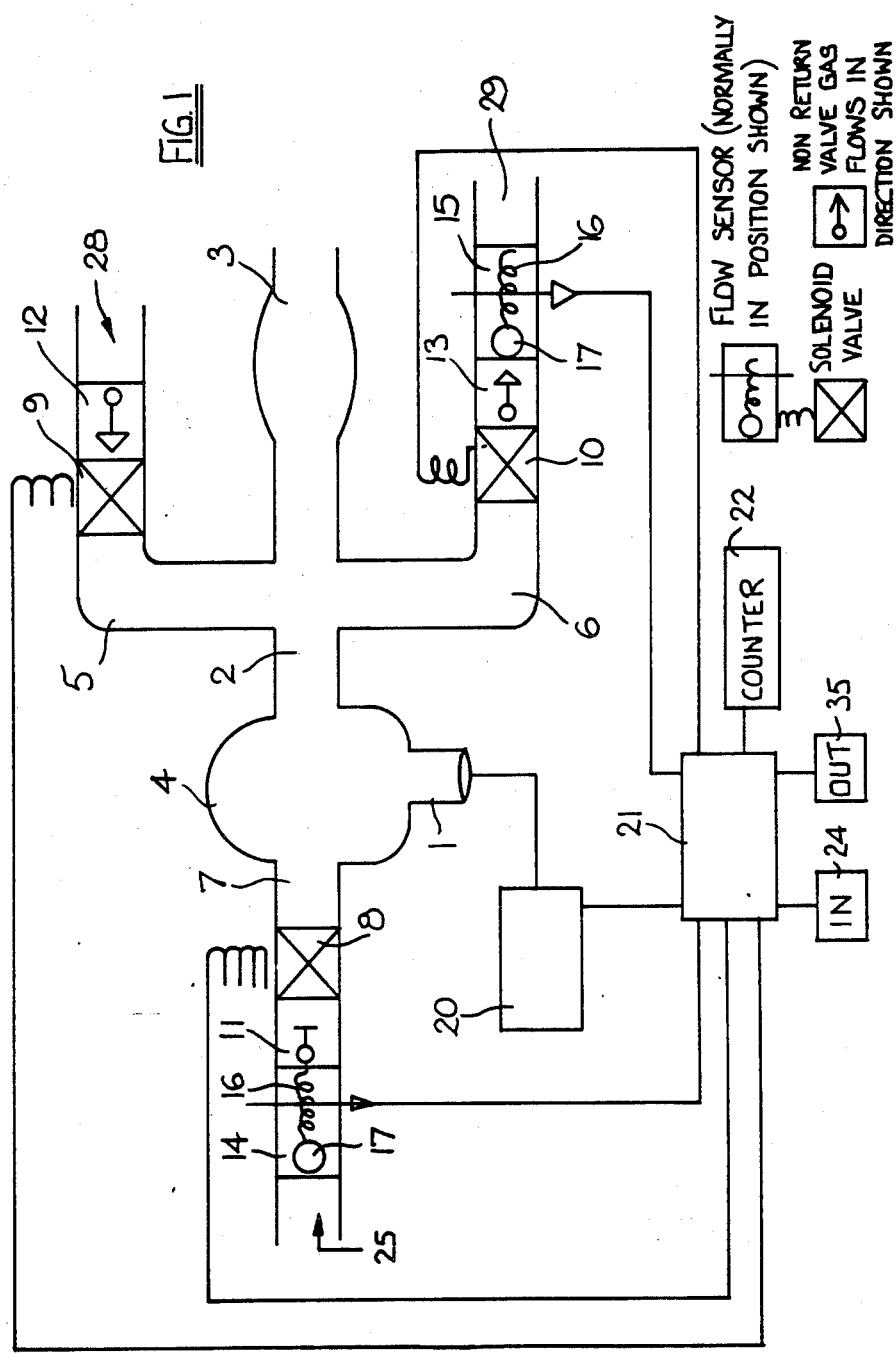
FIG. 1 is a diagrammatic layout of a dispenser according to one preferred form of the invention.

Referring to the drawings a dispenser and/or a method of dispensing are provided as follows. The dispenser of FIG. 1 comprises a supply means to supply inhalable material in inhalable form. This may be, in particular, any known type of aerosol generator or aerosol propellant such as a nebulizer 1. The aerosol may be processed by baffles to remove particles above a selected size and particles removed may be fed back into the nebulizer 1.

Figure 2:
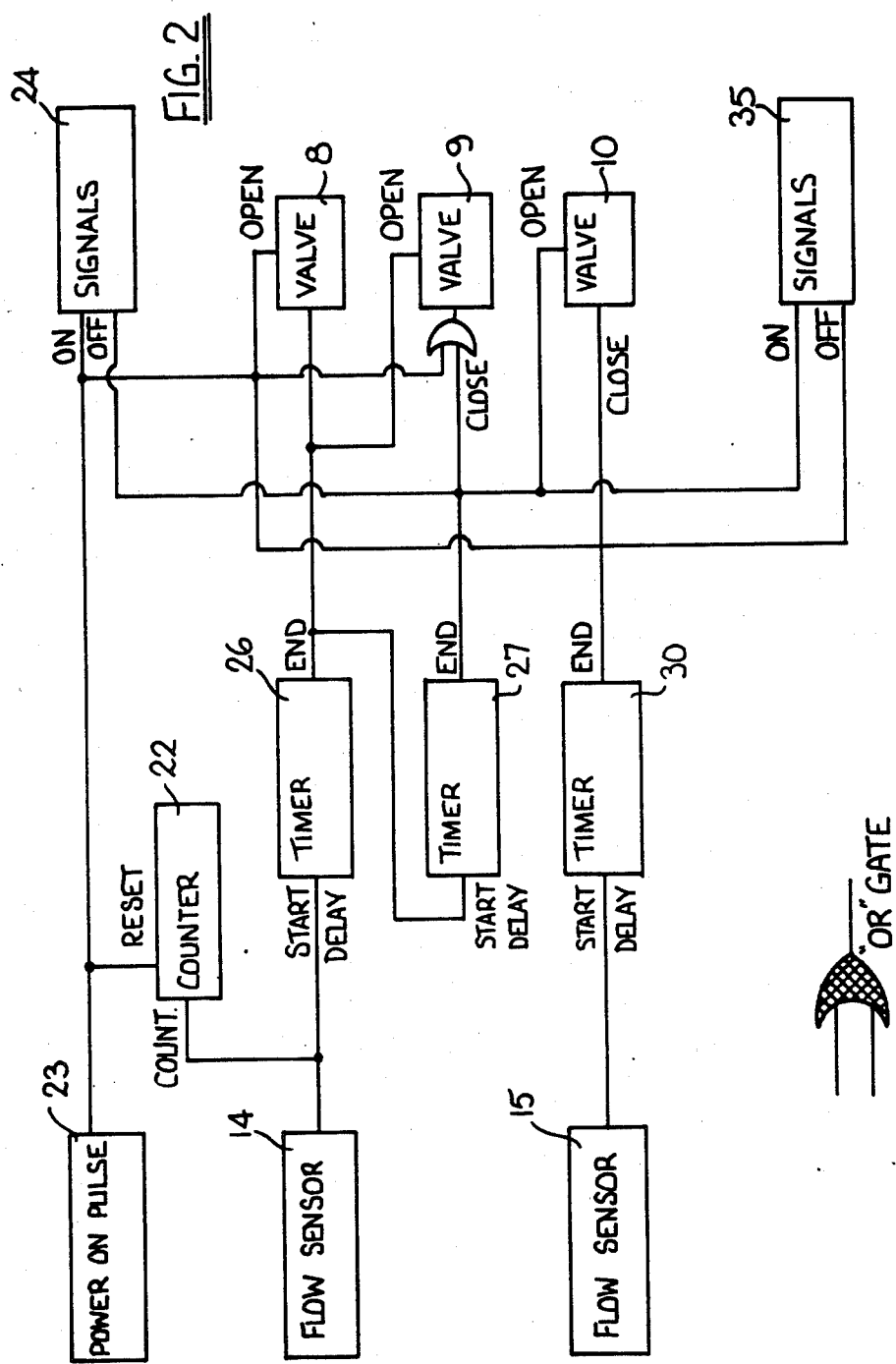
FIG. 2 is a simplified circuit block diagram of a control unit with the dispenser of FIG. 1.

Referring to FIGS. 1 and 2 a conduit 2 is provided from the nebulizer 1 to a mouth or nose piece 3 and the conduit 2 may lead from a cloud chamber or aerosol reservoir 4. Thus particles produced by the nebulizer 1 may pass through the reservoir 4 along the conduit 2 to the mouth piece 3. A pair of branch conduits 5 and 6 may lead from the conduit 2 the conduit 5 allowing air to be inhaled and the conduit 6 allowing air to be exhaled. A conduit 7 extends from the chamber 4. Flow control means are provided in each conduit and thus a valve 8 is provided in conduit 7 a valve 9 in conduit 5 and a valve 10 in conduit 6. Associated with each valve 8, 9 and 10 is a non-return valve 11, 12 and 13 directed to allow air flow in only the desired direction. The valves 8, 9 and 10 are desirably electrically operated comprising for example solenoid valves.

Detecting means are provided to detect air flow at least in the conduits 6 and 7. Thus a detector 14 is provided in conduit 7 and a detector 15 in conduit 6. Each detector 14 and 15 preferably comprises a bobbin 17 which may be biased for example by a spring 16 which bobbin 17 moves in the conduit in response to air movement in that conduit. The movement may be detected desirably electronically for example by interuption of a light beam 18 across the conduit (as shown in FIG. 5) or relatively by some other means known in the art. As alternatives the detectors 14 and 15 could instead comprise thermocouples 36 or thermistors 37 with a sensing circuit 38, as seen in FIG. 6 or a device to measure an increased or decreased pressure relative to atmosphere at some point connected to the mouth piece 3.

The nebulizer 1 may if required be provided with a power source 20 for example electrical or pneumatic or otherwise as required and the power source 20 may be turned on by a control unit 21. A compressed air nubulizer must be turned on and off now and then, although this is not so important when ultrasonic nebulizer is used. This turning on may be for example at the start of inhalation through mouth piece 3 or at some time after this and may be turned off on the opening of the valve 8 if desired to enable a rest to be taken at the start of the inhalation signals.

Turning the production of aerosol on and off during breathing could also reduce the dose of drug given per breath and this would allow more breaths to be taken for a given dose and thereby achieve greater precision of doseage.

A counter 22 may be provided to keep a count of the number of breaths taken and this may be presettable so that for example an alarm sounds or the dispenser stops delivering aerosol after the required number of breaths have been taken. The counter may begin incrementing when the start of the inhalation is detected.

A power "on" pulse circuit 23 is provided and when the dispenser is turned "on" a signal is forwarded from power "on" pulse circuit 23 and signal circuitry 24 indicates by visual or audio means that a breath should be taken by the user. The valves 9 and 10 are closed and valve 8 is opened. This allows inhalation of aerosol formed by the nebulizer 1 in the reservoir 4 by the drawing of breath through the inlet port 25. The state of breathing is detreated and for example when the start of inhalation is detected by the detecting means comprising the flow sensor 14 timer 26 begins and after a preset delay the valve 8 is closed. At this time timer 27 is started and valve 9 is opened about this time and this together with the non-return valve 12 allows inhalation of air through the inlet 28. After timer 27 has run for its preset time valve 9 is closed and the inhale signals at 24 are turned off. The exhale signals at 35 are then turned on and valve 10 is opened which together with the non-return valve 13 allows exhalation through the outlet port 29. When the start of exhalation is detected by the flow sensor 15 timer 30 is started and after this has run for its preset time the valve 10 is closed and the exhale signals from generator 35 are turned off. The inhale signals from generator 24 are then turned on and the valve 8 opens to restart the cycle when inhalation occurs.

Figure 3:
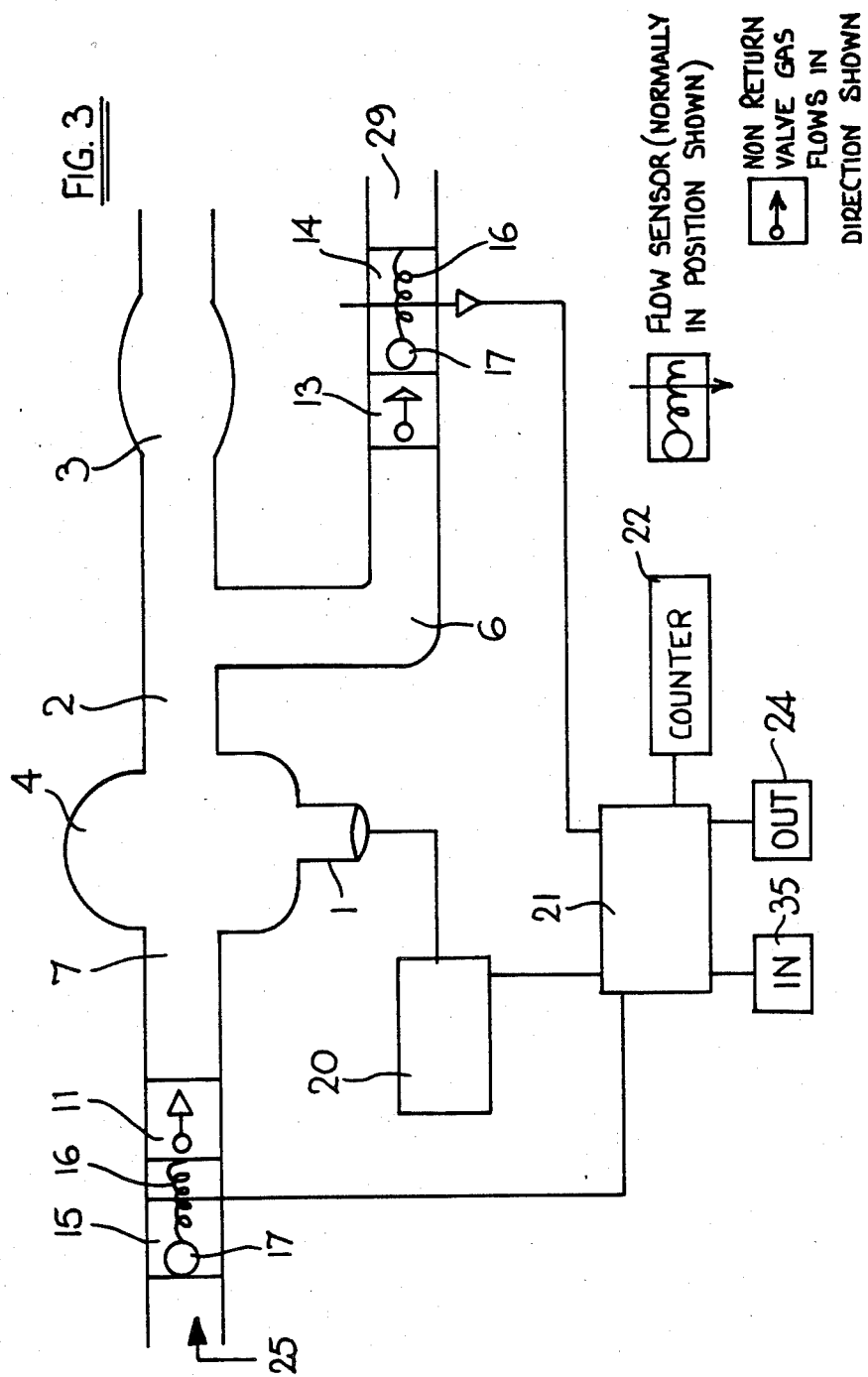
FIG. 3 is a layout as for FIG. 1 of an alternative form of the invention.
Figure 4:
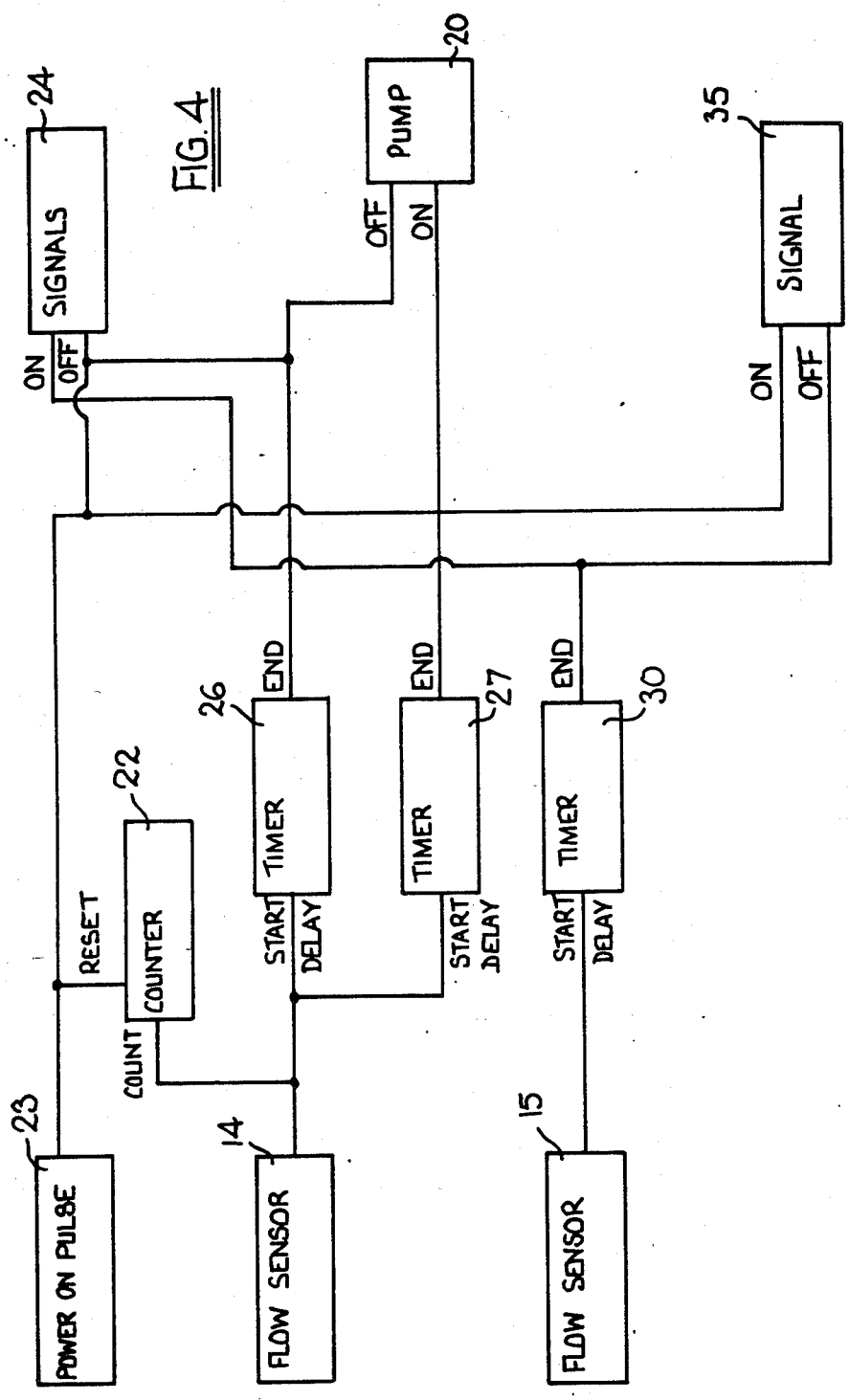
FIG. 4 is a circuit block diagram of a control unit as for FIG. 2 for the dispenser of FIG. 3.

In the embodiment of FIGS. 3 and 4 a compressed air nebulizer is used, which is able to be switched on and off and the intermittant nature of the operation allows selection of the running period to achieve a desired result. A conduit 2 is provided from the nebulizer 1 to a mouth piece 3 and the conduit 2 may lead from a cloud chamber or aerosol reservoir 4. Thus particles produced by the nebulizer 1 may pass through the reservoir 4 along the conduit 2 to the mouth piece 3. A branch conduit leads from the conduit 2 which allows air to be exhaled. A conduit 7 extends from the chamber 4. Non-return valves 11 and 13 allow air flow in only the desired direction.

Detecting means are provided to detect air flow at least in the conduits 6 and 7. Thus a detector 14 is provided in conduit 6 and a detector 15 in conduit 7. Each detector 14 and 15 preferably comprises a bobbin 17 which may be biased for example by a spring 16 which bobbin 17 moves in the conduit in response to air movement in that conduit. The movement may be detected desirably electronically for example by interruption of a light beam across the conduit or relatively by some other means. As alternatives the detectors 14 and 15 could comprise thermocouples or thermistors with a sensing circuit or a device to measure an increased or decreased pressure relative to atmosphere at some point connected to the mouth piece 3.

The nebulizer 1 may if required be provided with a power source 20 for example electrical or pneumatic or otherwise as required and the power source 20 may be turned on by a control unit 21. This turning on may be for example at the start of exhalation through mouth piece 3 or at some time after this and may be turned off at some time after this.

Again a counter 22 may be provided to keep a count of the number of breaths taken and this may be presettable so that for example an alarm sounds or the dispenser stops delivering aerosol after the required number of breaths have been taken. The counter may begin incrementing when the start of the inhalation is detected.

A power on pulse circuit 23 is provided and when the dispenser is turned "on" a signal is forwarded from power on pulse circuit 23 and signal circuitry 35 indicates by visual or audio means that a breath should be taken by the user. This allows inhalation of aerosol formed by the nebulizer 1 in the reservoir 4 by the drawing of breath through the inlet port 25. When the start of inhalation is detected by the detecting means comprising the flow sensor 15 timer 30 begins. After timer 30 has run for its preset time the exhale signals at 24 are then turned on which indicates that the user should exhale and signals at 35 are turned off. When the start of exhalation is detected by the flow sensor 14 timer 26 and timer 27 are started. After timer 27 has run for its preset time the aerosol generator is turned on. After timer 26 has run for its preset time the aerosol generator is turned off and signals at 24 are turned off and signals at 35 turned on. When inhalation occurs the timer 30 is started to repeat cycle.

In use the nebulizer 1 can be used to generate an aerosol of material such as insulin but which clearly could comprise other materials such as for example drugs for use in the treatment of asthmatic conditions. The drug used may dictate whether a compressed air or ultrasonic nebulizer is used.

Thus it can be seen that at least in the preferred form of the invention a dispenser and/or a method of dispensing are provided which have the advantage that the drug in aerosol form is released at that stage of the breath cycle where it is most efficaceous and is withheld at other times. In general this will be at the beginning of the inhalation of the breathing cycle and the invention has been described in relation to such a construction. The provision of signals to which the user matches his breathing also tends to ensure that the breath is held for a sufficient time for the aerosol particles to settle in the lungs. The rate of breathing may also be controlled and in particular decreased resulting in deeper breathing and thereby increased deposition of the aerosol particles in the lower lung.

What we claim is:

1. A dispenser, comprising:
   a supply means to supply inhalable material in inhalable form;
   a mouthpiece;
   said supply means being in communication with the atmosphere and said mouth piece;
   a flow control means to selectively allow or substantially prevent flow between said supply means and said mouth piece and between said supply means and the atmosphere;
   a signalling means to indicate to the user when to inhale and subsequently when to exhale;
   a first detection means to detect the commencement of inhalation and to cause a first timer to time a predetermined inhalation period, said first detection means also causing said flow control means to permit said inhalable material to move from said supply means to said mouth piece during a predetermined part of said period of inhalation, and to substantially prevent further inhalation at the end of said inhalation period; and
   a second detection means to detect the commencement of exhalation subsequent to the end of the period of inhalation and to cause a second timer to time a predetermined exhalation period.

2. A dispenser as claimed in claim 1 wherein said flow contol means also substantially prevents further exhalation at the end of said exhalation period.

3. A dispenser as claimed in claim 1 wherein said supply means comprises an aerosol generator.

4. A dispenser as claimed in claim 3 wherein said aerosol generator comprises a nebulizer.

5. A dispenser as claimed in claim 3 wherein said supply means comprises an aerosol propellant.

6. A dispenser as claimed in claim 3 wherein control means are provided to control said aerosol generator means, at least some operations of said control means being initiated by said detection means.

7. A dispenser as claimed in claim 6 wherein a branch conduit is provided to allow breath to be exhaled.

8. A dispenser as claimed in claim 1 wherein control means are provided to control said flow control means, at least some operations of said control means being controlled by said first detection means and at least some operations of said control means being controlled by said second detection means.

9. A dispenser as claimed in claim 1 wherein conduits are provided between said supply means and atmosphere and between said supply means and said mouthpiece and wherein a pair of branch conduits are provided extending from said conduits between said supply means and said mouthpiece, and said branch conduit allowing inhalation other than past said supply means and the other said branch conduit being provided to allow breath to be exhaled.

10. A dispenser as claimed in claim 9 further comprising non-return valves which allow breathing in a single direction only in said conduit and said branch conduits.

11. A dispenser as claimed in claim 1 wherein said detection means comprise a bobbin moved by the breath of the patient and a light beam disposed such that said bobbin can interrupt said light beam.

12. A dispenser as claimed in claim 1 wherein said flow control means comprise at least one of a thermocouple and a thermistor with at least one of a sensing circuit and a means for measuring any change in pressure relative to atmospheric pressure.

13. A dispenser as claimed in claim 1 wherein said signalling means comprise a means to generate humanly perceptible signals to said user.

14. A method of dispensing inhalable material comprising the steps of indicating to a patient that a breath should be taken, detecting the start of inhalation, causing inhalable material to be supplied to the air passages of the patient during a selected part of the period of inhalation, after a predetermined inhalation period substantially preventing further inhalation, indicating to the patient that exhalation should begin, detecting the start of exhalation and after a predetermined exhalation period again indicating that a breath should be taken.

15. A method of dispensing inhalable material as claimed in claim 14 including the further step of substantially preventing further exhalation when said predetermined exhalation period has ended.

16. A method of dispensing inhalable material as claimed in claim 14 wherein said selected part of the period of inhalation is towards the beginning of the period of inhalation.

* * * * *